(12) United States Patent
Dalemans et al.

(10) Patent No.: US 6,500,432 B1
(45) Date of Patent: Dec. 31, 2002

(54) METHOD TO ENHANCE AN IMMUNE RESPONSE OF NUCLEIC ACID VACCINATION

(75) Inventors: Wilfried Dalemans, Hoegaarden (BE); Marcelle Van Mechelen, Wagnelee (BE); Claudine Bruck, Rixensart (BE); Martin Friede, Farnham (GB)

(73) Assignee: SmithKline Beecham Biologicals, S.A., Rixensart (BE)

( * ) Notice: Subject to any disclaimer, the term of this patent is extended or adjusted under 35 U.S.C. 154(b) by 0 days.

(21) Appl. No.: 09/581,368

(22) PCT Filed: Dec. 11, 1998

(86) PCT No.: PCT/EP98/08152

§ 371 (c)(1),
(2), (4) Date: Jun. 12, 2000

(87) PCT Pub. No.: WO99/30733

PCT Pub. Date: Jun. 24, 1999

(30) Foreign Application Priority Data

Dec. 16, 1997 (GB) ................................................ 9726555

(51) Int. Cl.$^7$ .......................... A61K 39/00; A61K 48/00
(52) U.S. Cl. ........................... 424/184.1; 514/2; 514/44
(58) Field of Search ..................... 514/2, 44; 424/184.1

(56) References Cited

U.S. PATENT DOCUMENTS 6,111,068 A * 8/2000 Zimmerman et al. ....... 530/324

FOREIGN PATENT DOCUMENTS

WO  WO 96/40066  12/1996
WO  WO 97/28818  8/1997

OTHER PUBLICATIONS

Letvin, Norman L. et al. "*Potent protective anti–HIV immune responses generated by bimodal HIV envelope DNA plus protein vaccination.*" Proceedings of the National Academy Of Sciences, USA, vol. 94, pp. 9378–9383, Aug. 1997.

Okuda, Kenji et al. "*DNA vaccination followed by macro-molecular multicomponent peptide vaccination against HIV–1 induces sgrong antigen–specific immunity*" Vaccine, vol. 15, No. 10, Jul. 1, 1997, pp. 1049–1056.

Vaccine, vol. 15, No. 3, p. 340 (1997) "*Pharmaceutical materials for treatment of papilloma virus–associated lesions; interleukin–12 expression using a recombinant her-pes virus with vaccinia virus antigen for application as a recombinant vaccine*".

Barnett et.al.; Vaccination with HIV–1 gp120 DNA induces immune responses that are boosted by a recombinant gp120 protein subunit, 1997, Vaccine, vol. 15: 869–872.*

Coombes et al., Vaccine 14 (15): 1429–1438, Oct. 1996.*

Dorland's Illustrated Medical Dictionary, W.B. Saunders Co., Phila., PA, 1994, p. 1787.*

McCluskie, et al., 1999. Molecular Medicine, vol. 5, pp. 287–300.*

Liljeqvist, et al., 1999. Journal of Biotechnology, vol. 73, pp. 1–33.*

* cited by examiner

*Primary Examiner*—Scott D. Priebe
(74) *Attorney, Agent, or Firm*—William R. Marjarian; Stephen Venetianer; Charlie M. Kinzig

(57) ABSTRACT

This invention provides a method to enhance an immune response of nucleic acid vaccination by simultaneous administration of a polynucleotide and a polypeptide of interest.

2 Claims, 6 Drawing Sheets

Fig. 4.

METHOD TO ENHANCE AN IMMUNE RESPONSE OF NUCLEIC ACID VACCINATION

FIELD OF THE INVENTION

This invention relates to a method to enhance an immune response of nucleic acid vaccination by simultaneous administration of a polynucleotide and a polypeptide of interest.

BACKGROUND OF THE INVENTION

In 1990 Wolff and colleagues (Wolff et al., *Science* 247:1465–1468 (1990)) reported that nonreplicating plasmid DNA encoding reporter genes could be internalized by muscle cells, without the use of any transfection vehicle, and that the encoded proteins were expressed following injection of the plasmid DNA. The subsequent finding that the expressed protein of "naked" (i.e., devoid of agents which promote transfection) plasmid DNA was immunogenic upon intramuscular inoculation has opened a new area of research with significant clinical impact.

As such, vaccination with nucleic acids (NAVAC) has become a relatively new approach for vaccinating against a multitude of diseases. It involves the in vivo production of a polypeptide within a host cell rather than the more conventional method of administering a polypeptide (or an attenuated, or killed microorganism) that was first produced (or cultured) in vitro. NAVAC also differs from more conventional vaccines in that the compound administered consists of nucleic acids, i.e., DNA or RNA, encoding selected antigen(s). Upon injection of these nucleic acids, they are taken up by the recipient cells of a mammalian host and the antigen encoded by such nucleic acid(s) is subsequently expressed. Thereafter, the presence of a foreign antigen within a host can elicit a specific immune response directed against the antigen. It has been shown that NAVAC induces humoral, i.e., antibodies, as well as cell mediated immunity, i.e., T helper cell responses and cytotoxic lymphocytes (see, e.g., Corr et al., *J. Exp. Med.* 184:1555–1560 (1996); Doe et al., *Proc. Nail. Acad. Sci.* 93:8578–8583 (1996)).

The induced immune responses have been shown to protect against a subsequent challenge with the infectious organism from which the antigen was originally obtained in a certain number of animal models (e.g. Ulmer et al., *Science* 59:1745–1749 (1993); Sedegah et al., *Proc Natl Acad Sci USA* 91:9866–9870 (1994); Manickan et al., *J. Inmmunol.* 155:259–265 (1995)). NAVAC has been shown to be much less efficient in larger animal species (when compared to administration of adjuvanted proteins), and large amounts of DNA have to be administered to achieve immunisation levels comparable to that found in smaller animal species, e.g., mice (Gramzinski et al., *Vaccine Research* 5:173–183 (1996); Lu et al., *J. Virol.* 70:3978–3991 (1996); Shiver et al.; *Joumal of Pharmaceutical Sciences* 85:1317–1324 (1996)). There is thus a need to improve the efficacy of NAVAC, for example, by developing new delivery and targeting mechanisms, new adjuvantation techniques, other routes of administration, etc. It is the object of this invention to provide another improvement to the efficacy of DNA vaccination.

SUMMARY OF THE INVENTION

In one aspect, the present invention provides a method for enhancing the immune response of a nucleic acid vaccination by administration of (i) a polynucleotide encoding a gene of interest, which encodes a polypeptide and (ii) by also administering the polypeptide simultaneously, that is, during the same ongoing immune response. Preferably the administration of polynucleotide and polypeptide occur within 0–10 days of each other. One preferred embodiment is administration of polypeptide 3–7 days prior to administration of polynucleotide. The polypeptide may be further prepared prior to administration such that it is presented to the immune system in such a way to provide a delayed release (e.g., encapsulated). In such a case, the polypeptide is preferably administered at the same time (concurrently) as the polynucleotide.

In another aspect, the present invention provides a method for enhancing the immune response of a polypeptide vaccination by administration of a nucleotide encoding a gene of interest, which encodes a polypeptide of interest, and by also administering the polypeptide simultaneously, that is, during the same ongoing immune response.

In further related aspects, the present invention relates to pharmaceutical compositions, vaccines, and methods to prepare such compositions and vaccines, comprising a polynucleotide encoding a gene of interest, and the corresponding polypeptide of interest, where the ratio of polynucleotide to polypeptide is from 1000:1 to 1:1 (w/w). Optionally, the polypeptide is prepared prior to administration such that it is presented to the immune system in such a way to provide a delayed release.

DETAILED DESCRIPTION OF THE INVENTION OF THE INVENTION

The present invention relates to a method for enhancing the immune response of a mammal (e.g., mice, rabbits, primates, man) to DNA vaccines by admixing two different compounds prior to simultaneous administration. The first compound comprises a polynucleotide (nucleic acid) such as DNA or RNA which encodes a selected polypeptide that can stimulate protective immunity. The second compound comprises a polypeptide, which preferably is the same polypeptide (or substantially the same, i.e., having the same immunodominant epitope(s)) encoded by the nucleic acid of this invention. The enhancement relates to the total increase in immune response, as determined by both humoral and cell mediated immune responses. That is, there are measurable increases in one or more of the following: total antibody titer (to the selected polypeptide); in lymphoproliferation; and in CTL (cytotoxic T lymphocyte) levels. Moreover, when nucleic acid such as DNA encoding the gene of interest is admixed with the corresponding polypeptide and (simultaneously) administered to a mammal, a synergistic effect is observed. That is, not only is the DNA vaccine capable of inducing an immune response in the presence of protein (polypeptide), but the presence of such protein (polypeptide) has been found to actually enhance the efficacy of the DNA vaccine. Thus, one aspect of the present invention is a composition comprising a polynucleotide and polypeptide for enhancing an immune response. Optionally, the polypeptide may be adjuvanted as well.

Conversely, the presence of specific nucleic acid (e.g., DNA encoding the whole or substantial parts of the polypeptide) to a polypeptide vaccine was found to increase that immune response as well. That is, the interaction of a DNA/polypeptide mixture enhances the efficacy of either individual component. This enhancement is specific to the polynucleotide added, as a similar polynucleotide not encoding the specific polypeptide was unable to enhance the immune responses. One surprising aspect of the instant invention was the fact that the DNA component and the polypeptide component did not compete with each other in eliciting an immune response, and that, to the contrary, a synergistic effect was observed when DNA and protein were administered simultaneously.

The present invention differs from the "prime boost" approach (Barnett et al., *Vaccine* 15:869–873 (1997)) where two distinct vaccine preparations (one DNA, one protein) are prepared and administered separately, at different times, and in a specific order. That is, under the prime boost approach, a DNA molecule is administered to "prime" the immune system and at some subsequent time (weeks or months later) after the primary immune response is established a protein is administered to boost the then pre-existing immune response.

Another benefit of the present invention is that in certain cases, where there is a predisposition to a strong immune response (e.g., high percentage of responders to initial vaccination, high level of antibody titers, CTL response, etc.), the combination of both compounds (DNA+protein) can obviate the need for immunostimulants.

In a further embodiment of this invention are included formulations wherein the nucleic acid and protein antigen are co-administered (preferably simultaneously), but the protein antigen is encapsulated within a delayed-release vehicle which liberates the protein antigen several days after administration. Such formulations enhance the magnitude of the induced immune response compared to nucleic acid alone, without biasing the immune response.

Nucleic Acid

The polynucleotide materials used according to the present invention comprise DNA or RNA sequences coding for polypeptides that have useful therapeutic application, e.g., prophylactic or therapeutic vaccines. According to the methods of the invention, both expressible DNA and RNA can be delivered to cells to form therein a polypeptide translation product. If the nucleic acids contain the proper control sequences, they will direct the synthesis of relatively large amounts of the encoded protein. Preferably they encode antigens for organisms associated with infectious diseases caused by viruses (including but not limited to Hepatitis (all forms), HSV, HIV, CMV, EBV, RSV, VZV, HPV, polio, influenza), parasites (e.g., from the genus Plasmodium), and pathogenic bacteria (including but not limited to *M. tuberculosis, M. leprae*, Chlamydia, Shigella, *B. burgdorferi*, enterotoxigenic *E. coli, S. typhosa, H. pylon, V. cholerae, B. pertussis*, etc.). Other antigens, such as found on cancerous cells (examples of known targets for immune responses to tumors are e.g., E7 for HPV-induced cervical carcinoma, Her-2/neu for breast and other cancers, MAGE-3 for melanoma and other cancers, tyrosinase, melanA/MART, or gp100, a melanocyte-specific differentiation antigen) are also contemplated within the scope of this invention.

The polynucleotides of the present invention may be in the form of linear fragments, or non-linear fragments integrated into plasmids or viral DNA. The polynucleotides (or nucleic acids) may be associated with other materials which promote transfection such as liposomal formulations, charged lipids (cationic or anionic: e.g., Lipofectin™, Transfecta™, DOTAP™, cochleates), polycations (e.g., polylysine, polyethylenimine, etc.), viral proteins (e.g., histones), peptides that bind to nucleic acids (e.g., condensing agents), dendrimers, PLPG nicroparticles, etc.

Where the nucleic acid is DNA, promoters suitable for use in various mammalian systems are well known. For example, suitable promoters include CMV IE, RSV LTR, SV40, Adeno MLP, metallothionein, etc.

The exact cellular and immunological mechanisms underlying the induction of the immune response by NAVAC are not yet completely understood. A hallmark of NAVAC is the induction of cytotoxic responses, which is a part of the immune response that is difficult to induce by protein (vaccination) approaches. In order to induce a CTL response, the antigen must be presented in the context of MHC-I molecules present within the cell. Since in NAVAC the protein is expressed intracellularly, such MHC-I presentation is readily achieved. Thus, nucleic acid vaccination is particularly well suited for stimulating cellular immunity, in particular, cytotoxic T cell responses to an antigen of interest.

Protein

The protein can be any polypeptide that has a useful therapeutic application, e.g., as a prophylactic or therapeutic vaccine. As noted above, the present invention is not limited to a particular polypeptide, however, it would be desirable to target proteins that may not intrinsically stimulate a strong cell mediated immunity response, such as polypeptides found in intracellular pathogens (for example, but not limited to *M. tuberculosis, M. Ieprae*, Chlanzydia), certain tumor-specific antigens (e.g., found on breast or colon cancer), and weakly inmnunogenic viral proteins (e.g., from Herpes, EBV, CMV, HPV, etc.).

It is noted that a potential drawback of recombinant proteins and subunit vaccines is the fact that glycoprotein antigens may need to be presented in a specific conformation (i.e., identical to the native protein) to elicit an immunoprotective response. When purified from recombinant expression systems, it is sometimes difficult to insure that the antigens are conformationally correct. However, the introduction of a gene encoding an antigen in vivo and its subsequent intracellular expression will insure that the protein product is synthesized, modified and processed very similar to the native pathogen protein. Thus, for example, the expression of a gene for a human viral glycoprotein will likely result in the correct conformation of the antigen. As a consequence, the native antigenic epitopes will be presented to the immune system and can result, for example, in the generation of neutralizing antibodies specific to the native viral glycoprotein.

DNA+Protein

Normally a DNA vaccination elicits a predominantely Th1 helper type response. Conversely, most soluble non-particulate antigen (i.e., protein based) vaccines elicit a predominately Th2 response. Once "primed", the immune system response remains predominately Th1 or Th2, depending on the composition (i.e., nucleic acid or polypeptide) used for the initial vaccination. Quite unexpectedly the combination of DNA+protein, when administered simultaneously, exhibits a more balanced Th1+Th2 response. That is, both responses are elicited and the combination of polynucleotide/polypeptide appears to act synergistically. Moreover, the induction of CTL's is not hampered by the presence of the extracellular protein.

Based on the polynucleotide/polypeptide immune response, another advantage of the instant invention is that this approach provides a method to treat latent viral infections. Several viruses (for example members of the Herpes virus group, etc.) can establish latent infections in which the virus is maintained intracellularly in an inactive or partially active form. There are few ways of treating such infections. However, by inducing a cytolytic immunity against a latent viral protein, the latently infected cells can eventually be targeted and eliminated. Thus, by administering a polynucleotide/polypeptide composition, this effect should be enhanced over pure NAVAC (i.e., nucleotide only) approach since a stronger immune response, including cytolytic activity, can be established.

A related application of this approach is to the treatment of chronic pathogen infections. There are numerous examples of pathogens which replicate slowly and spread directly from cell to cell. These infections are chronic, in some cases lasting years or decades. Examples of these are the slow viruses (e.g. Visna), Hepatitis B, the Scrapie agent and HIV. Other examples of pathogens include organisms of the genus Plasmodium, Mycobacterium, Helicobacter, Borrelia, and Toxoplasm and well as others as noted above.

Finally, this approach may also be applicable to the treatment of malignant disease. For example, vaccination to mount a strong immune response including a T-cell mediated component to a protein expressed by the tumor cell, will potentially result in the elimination of these cells.

As used above, "simultaneous" administration refers to the same ongoing immune response. Preferably both compositions are administered at the same time (concurrent administration of both DNA+protein), however, one compound could be administered within a few week's time (preferably 1–10 days) of the other (initial) administration and still be considered as "simultaneous" since they both act during the same ongoing immune response. Normally, when a polypeptide is administered, the immune response is considered immediate in that an immune response will initiate as soon as the antigen is exposed to the immune system. In contrast, when nucleic acid is administered, peak antigen expression (in vivo) is observed 3–7 days after administration, and thus antigen exposure to the immune system is considered "delayed" when compared to the kinetics of protein vaccination. Regardless of this difference in kinetics, co-administration of nucleic acid and polypeptide can be considered "simultaneous" by understanding that they are both functionally present during the process of an ongoing immune response. In order to present both antigenic forms (i.e. polypeptide as such and polypeptide expressed by the administered polynucleotide), virtually simultaneously to the immune system, formulations can be conceived wherein the polypeptide is contained in such a way that its release from the formulation is delayed after the administration. This allows the expression of polypeptide from the polynucleotide to occur first, which is then subsequently complemented by the delayed released polypeptide from the formulation.

Thus another aspect of the present invention is the concurrent admirnistration of both DNA+protein where the protein (polypeptide) is present or administered in the form of delayed-release particles intended to hide the antigen from the immune system for a short period of time. Preferably it is 1–10 days.

Regardless of the different modes or possibilities of "simultaneous" administration as described above, it is key to the invention that both antigenic substrates are present during the induction phase of an ongoing immune response. In comparison to this, the prime boost concept refers to 2 separate immune responses: (i) an initial priming of the immune system with a polynucleotide followed by (ii) a secondary or boosting of the immune system with a polypeptide many weeks or months after the primary immune response has been established.

The DNA+protein complex can thus be administered as two separate events or combined (admixed) to permit one administration. Preferably, the DNA+protein are admixed. Admixing can occur just prior to use, or when the two components are manufactured (and formulated), or any time in between.

The compositions and vaccines of the invention comprise DNA+protein (polypeptide) in a ratio of 1000:1 (i.e., 1 mg DNA/1 ug protein) to 1:1 to 1:100 (w/w). Preferably it is in the range of 100:1 to 1:1. More preferably it is in the range of 20:1 to 1:1. One preferred ratio is 5:1.

Adjuvants

The polynucleotides, polypeptides and polynucleotide+polypeptide mixture (complex) of the present invention, when adjuvanted, are preferably adjuvanted in the vaccine formulation of the invention. Vaccine preparation is generally described in *New Trends and Developments in Vaccines*, Voller et al. (eds.), University Park Press, Baltimore, Md., 1978. Fullerton describes encapsulation within liposomes, U.S. Pat. No. 4,235,877. Suitable adjuvants include an aluminum salt such as aluminum hydroxide gel (alum), aluminum phosphate, or algannmulin , but may also be a salt of calcium, iron or zinc, or may be an insoluble suspension of acylated tyrosine, or acylated sugars, cationically or anionically derivatised polysaccharides, or polyphosphazenes.

Suitable adjuvant systems include, for example, a combination of monophosphoryl lipid A, preferably 3-de-O-acylated monophosphoryl. lipid A (3D-MPL) together with an aluminum salt. An enhanced system involves the combination of a monophosphoryl lipid A and a saponin derivative particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21 3D-MPL & tocopherol in an oil in water emulsion is described in WO 95/17210 and is a preferred formulation. In addition, the DNA could serve as an adjuvant as well by encoding the gene of interest and CpG sequences. Such CpG sequences, or motifs, are known in the art.

Formulations

Administration of pharmaceutically acceptable salts of the polynucleotides and proteins described herein is included within the scope of the invention. Such salts may be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic nontoxic bases include salts of primary, secondary, and tertiary amines, basic amino acids, and the like. For a helpful discussion of pharmaceutical salts, see S. M. Berge et al., *J Pharm Sci* 66:1–19 (1977), the disclosure of which is hereby incorporated by reference.

The protein component of the formulation may be administered in the form of delayed-release particles intended to hide the antigen from the immune system for several days, and to then liberate the antigen. In doing so the protein antigen is liberated once the DNA has initiated the priming of the immune response. The concept of using delayed-release formulations for achieving both priming and boosting of the immune response with protein antigens has been discussed in the literature, for example see Coombes, A. et al. (Vaccine, 14:1429–1438 (1996)). Most published attempts at achieving delayed-release formulations of protein antigens have used microparticles composed of poly (lactide-co-glycolide) in which the protein antigen is entrapped. Other formulations have been prepared with polyacrylate, latex, starch, cellulose and dextran. Another type of carrier that can be used as a delayed delivery vehicles (i.e., for delayed release formulations) are supramolecular biovectors (SMBVs). SMBVs comprise a non-liquid hydrophillic core, such as a cross-linked polysaccharide or a cross-linked oligosaccharide and, optionally, an external layer comprising an amphiphillic compound, such as a phospholipid. See, for example, U.S. Pat. No. 5,151,264, PCT applications WO94/20078, WO94/23701 and WO96/06638.

In a preferred embodiment of the invention the protein antigen is adsorbed to alum, and the alum particles are then coated with a bio-degradeable polymer such as poly(caprolactone) or poly(lactide-co-glycolide). Unlike published methods for encapsulating protein antigen, such formulations provide a hermetic layer of polymer around the antigen, preventing antigen liberation for a period of time ranging from a day to several weeks.

Polynucleotides and proteins for injection, a preferred route of delivery, may be prepared in unit dosage form in ampoules, or in multidose containers. The polynucleotides and proteins may be present in such forms as suspensions, solutions, or emulsions in oily or preferably aqueous vehicles. Alternatively, the polynucleotide salt may be in lyophilized form for reconstitution, at the time of delivery, with a suitable vehicle, such as sterile pyrogen-free water. Both liquid as well as lyophilized forms that are to be reconstituted will comprise agents, preferably buffers, in amounts necessary to suitably adjust the pH of the injected solution. For any use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of polynucleotide and proteinaceous material.

The unit dosage ampoules or multidose containers, in which the polynucleotides and polypeptides are packaged prior to use, may comprise an hermetically sealed container enclosing an amount of polynucleotide (and/or polypeptide) or solution containing a polynucleotide (and/or polypeptide) suitable for a pharmaceutically effective dose thereof, or multiples of an effective dose. The polynucleotide and polypeptide are packaged as a sterile formulation, and the hermetically sealed container is designed to preserve sterility of the formulation until use.

Dosage and Route of Administration of DNA/Protein Complex

The polynucleotides may be delivered to various cells of the animal body, including for example, muscle, skin, brain, lung, liver, spleen, or to the cells of the blood. Administration of the polynucleotide/protein complex is not limited to a particular route or site. For example, the route could be intramuscular, intradermal, epidermal (using for example a gene gun), intra pinna, oral, vaginal, nasal, etc. Preferably the route is intramuscular, intradermal or epidermal.

Preferred tissues to target are muscle, skin and mucous membranes. Skin and mucous membranes are the physiological sites where most infectious antigens are normally encountered. Skin associated lymphoid tissues contain specialized cells like keratinocytes, Langerhans' cells, and other dendritic cells which are involved in the initiation and further regulation of immune responses.

The dosage to be administered depends to a large extent on the condition and size of the subject being treated as well as the frequency of treatment and the route of administration. Regimens for continuing therapy, including dose and frequency may be guided by the initial response and clinical judgment. The parenteral route of injection into the interstitial space of tissues is preferred a preferred route, although other parenteral routes, such as inhalation of an aerosol formulation, may be required in specific administration, as for example to the mucous membranes for the nose, throat, bronchial tissues or lungs. In addition, oral administration may be used for vaccination against infectious diseases of mucosal surfaces such as the nose, lungs and sinuses. In preferred protocols, a formulation comprising the polynucleotide/protein complex in an aqueous carrier is injected into tissue in amounts of from 10 μl per site to about 5 ml per site. The concentration of polynucleotide/protein complex in the formulation is from about 0.1 μg/ml to about 20 mg/ml, and preferably in the range of 100–1000 ug/ml.

EXAMPLES

The examples below are carried out using standard techniques, which are well known and routine to those of skill in the art, except where otherwise described in detail. The examples are meant to illustrate, but not limit the invention.

Example 1

Vaccine Preparation

A. Plasmid DNA

The coding sequence of the RSV-F protein (Collins et al., *Proc. Natl. Acad. Sci.* 81:7683–7687 (1984)) (574 amino acids) was cloned into the eukaryotic expression vector JA4304 (Lu et al., *J. Virol* 70:3978–3991 (1996)) using cloning techniques well known by persons skilled in the art. Briefly, the RSV-F insert was cloned as a HindIII-EcoRV fragment into linearised JA4304 at the HindII and blunt-ended BgIII restriction sites. Recombinant plasmids were analyzed by restriction digests and were sequenced at the insertion sites. Plasmid DNA for injection was purified by Qiagen columns (Maxi-Prep), followed by two phenol/chloroform extractions, ether extraction, and ethanol precipitation. The plasmid DNA was resuspended into sterile water and stored at −20° C. Similarly, the coding sequence used to express the HSV gD protein (McGeoch et al., *J. Gen. Virol* 68: 13–38 (1987)) was contained in a HindIII-Bam HI-BglII double restriction fragment, cloned into JA4304 HindIII-BglII.

B. Protein

The coding sequence of the RSV F and G proteins (Huang et al., *Virus Res.* 2:157–173 (1985)) was cloned and a chimeric F/G protein was made. Very briefly, plasmid pEE14-FG containing a chimeric construct comprising of a fusion between amino acid sequences of F (1–526) and G (69–298) was received from a collaboration with A. BOLLEN (ULB/CRI, Belgium). This FG fusion protein contains a total of 755 amino acids. It starts at the N-terminal signal sequence of F and lacks the C-terminal transmembrane domain (526–574) of the F glycoprotein. Then, fused to the 3' end of the coding region is the extracellular region of G glycoprotein, lacking an amino-terminal region and a carboxy terminal region. The pEE14-FG expression plasmid was generated by the insertion of the FG coding sequence from pNIV2857 (A. Bollen, ULB/CRI, Belgium) as an Asp7181 (blunt) 5'-HindIII (blunt) 3' restriction fragment (2188 bp) into the SmaI site of pEE14 (Celltech). It will be appreciated that there are many of expression plasmids known in the art that can be used.

CHO K1 cells derived were transfected with 20 ug of pEE14-FG plasmid DNA twice CsCl purified using a Ca-phosphate/glycerol transfection procedure. Cell clones were selected according to the procedure of the GS (glutamine synthetase) expression system (Crocett et al., *BioTechniques*, 8:662 (1990)) and amplified in the presence of 25 micro molar methionine sulphoximine (MSX) in G MEM medium containing no glutamine and supplemented with 10% dialyzed FBS (Foetal Bovine Serum). Following transfection, 39 MSX resistant clones were screened in 24-well plates and their supernatants were tested for secretion of the FG fusion protein. All transfectants proved to be positive for F antigen expression using a specific 'Sandwich' ELISA assay (i.e., rabbit polyclonal anti FG serum/FG Antigen/mAb19). Monoclonal antibody 19 recognizes a conformational F1 epitope and is neutralizing.

The 3 best FG-producer clones (n°7, 13 and 37) were single-cell subcloned in a limiting dilution assay using 0.07 cells per well in a 96-well plates. A total of 59 positive subclones were obtained and the 16 best FG-producers were further characterized by western blot and ELISA. Again, the 8 best FG-subclones were further amplified and their FG expression was evaluated in presence and absence of sodium butyrate (2 mM) or DMSO (1 or 2%). Six subclones were amplified and cell vials were made and stored at −80° C. or in liquid $N_2$. Finally, the 3 best FG subclones were selected. These are CHOK1 FG °7.18, °13.1, and °37.2.

Western blot analyses (non-reducing conditions) with monoclonal mAb19 indicated a major band of FG at about 135 kDa.

The addition of Sodium butyrate in CHO-FG cell culture medium increased the expression level of FG 3 to 12 fold depending on the subclone and cell culture growth conditions. In particular, subclone CHO-FG 13.1 expressed FG protein 8–10 fold higher in the presence of butyrate.

Frozen cell culture supernatant is was thawed in the cold room (4° C.–7° C.). Protease inhibitors (for example, 1/1000 Aprotinin, 0.5 mg/litre leupeptin, 0.5 mM Pefabloc) are added. The thawed supernatant is loaded onto a column packed with Pharmacia SP Sepharose HP™ or fast flow resin. The SP Sepharose HP™ or fast flow resin is equilibrated with 20 mM MES pH 6.5, 1% thesit (buffer D). After loading, the column is washed with buffer D until the absorbance at 280 nrn returns to baseline. The column is eluted successively with buffer D containing 150 mM NaCl, than 300 mM NaCl and finally 1 M NaCl.

FG is eluted with buffer D containing 300 mM NaCl. The eluate could be, if necessary, concentrated on a Filtron OMEGA 30 or 50 kDa membrane. Eluate, whether concentrated or not, is loaded onto a Pharmacia Superdex 200™ 16/60 column equilibrated and eluted in PBS, 1% Tween 80. 1–3 mg of total protein (Lowry) are injected per run.

As noted, a truncated version of recombinant glycoprotein Herpes Simplex Virus (HSV) type 2 ($rgD_2t$) was also prepared. Such protein and DNA coding sequences are known in the art, see, e.g., EP 139 417B, U.S. 5,656,457, WO 92/16231.

Recombinant Human Immunodeficiency Virus type 1 (HIV-1) envelope glycoprotein gp120 was prepared. Gp120 expression and the DNA coding sequence is known in the art as well, see, e.g., U.S. Pat. Nos. 5,653,985, 5,614,612, EP 290 261B.

Example 2

Immunisation of Mice

A. Plasmid DNA Vaccination

Plasmid DNA (encoding the RSV-F protein "DNA F") was resuspended at a concentration of 10 µg/50 µl of sterile PBS just prior to injection. Anaesthetized mice were injected twice with 50 µl of this DNA vaccine into the tibialis anterior muscle; the booster injection was given four weeks after the first. In certain groups, the DNA vaccine was only given at the first injection.

B. Protein Vaccination

FG protein vaccine. The chimeric F/G protein ("FG") was prepared at a dose of 2 µg/50 µl by resuspending purified FG into 150 mM NaCl, 10 mM PO4 (pH 7.4). Phenoxyethanol was added as preservative at a concentration of 0.5%. The protein vaccine was prepared 7 days before the primary injection, and stored at 4° C.

C. Mixed DNA/Protein Vaccination

Seven days prior to the primary injection, 2 µg of FG per dose was mixed with 26.95 µl $H_2O$ and 4.25 µl of 1.5M NaCl, 100 mM PO4 (pH 7.4); in addition, 0.25 µl of phenoxyethanol was added as preservative. This preparation was stored at 4° C. Just prior to the respective injections (first or secondary), 5.651 µl of DNA (corresponding to 10 µg) encoding F was added to this protein preparation.

The immunisation scheme is presented below:

| First injection | Second (booster) injection |
|---|---|
| DNA F 10 µg | PBS |
| DNA F 10 µg | DNA F 10 µg |
| DNA F 10 µg | FG 2 µg |
| PBS | FG 2 µg |
| FG 2 µg | FG 2 µg |
| DNA F 10 µg + FG 2 µg | DNA F 10 µg + FG 2 µg |

Example 3

Serological Responses upon mixed Vaccine Administration

Mice were immunised twice with the mixed DNA/protein vaccine composition and the relevant controls, and their serological response was analysed using the following protocol.

3.a. Protocol: Enzyme-Linked ImmunoSorbent Assays (ELISA)

Maxisorp Nunc immunoplates were coated overnight at 4° C. with 50 µl/well of 1 µg/ml FG antigen diluted in PBS (rows B to H of the plate) or with 50 µl of 5 µg/ml purified goat anti-mouse immunoglobulin antiserum (Boehringer) diluted in PBS (row A-IgG standard curve). Saturation of the plates was done for 1 Hr at 37° C. with 100 µl/well of PBS BSA 1% Tween 200.1% NBCS 4% (saturation buffer). Then, serial, 2-fold dilutions of IgG (mouse polyclonal antiserum, SIGMA) in saturation buffer (50 µl per well) were put in rowA as standard starting at 200 ng/ml; serum samples were applied in rows B to H starting at a 1/50 dilution further serially 2-fold diluted; incubation was for 1 Hr30 at 37° C. Washing was done 3 times with PBS Tween 20 (0.1%). Then, biotinylated goat anti-mouse IgG antiserum (Amersham) diluted 5000× in saturation buffer was added (50 µg/well) and incubated for 1H30 at 37° C. After 3 washings as above and subsequent addition for 30 min at 37° C. of streptavidin biotinylated horseradish peroxydase complex (Amersham) diluted 1000× in saturation buffer (50 µl/well), plates were washed 5 times and incubated for 15 min at room temperature (in darkness) with 50 µl/well of substrate solution (OPDA 0.4 mg/ml and $H_2O_2$ 0.03% in 50 mM pH4.5 citrate buffer). The reaction was stopped by adding $H_2SO_4$ 2N (50 µl/well). The color reaction was read on a multiscan ELISA reader at wavelength 492/620 nm. Antibody titers were calculated by the 4 parameter mathematical method using SoftMaxPro software.

The same protocol was used to determine the specific isotype distribution of the antisera using mouse monoclonals (SIGMA) as standard and isotype-specific biotinylated goat anti-mouse IgG1,IgG2a and IgG2b antisera (Amersham) for the samples. The isotype distribution was expressed as the percentage of the total IgG specific immune response.

3.b. Results

Figure 1:
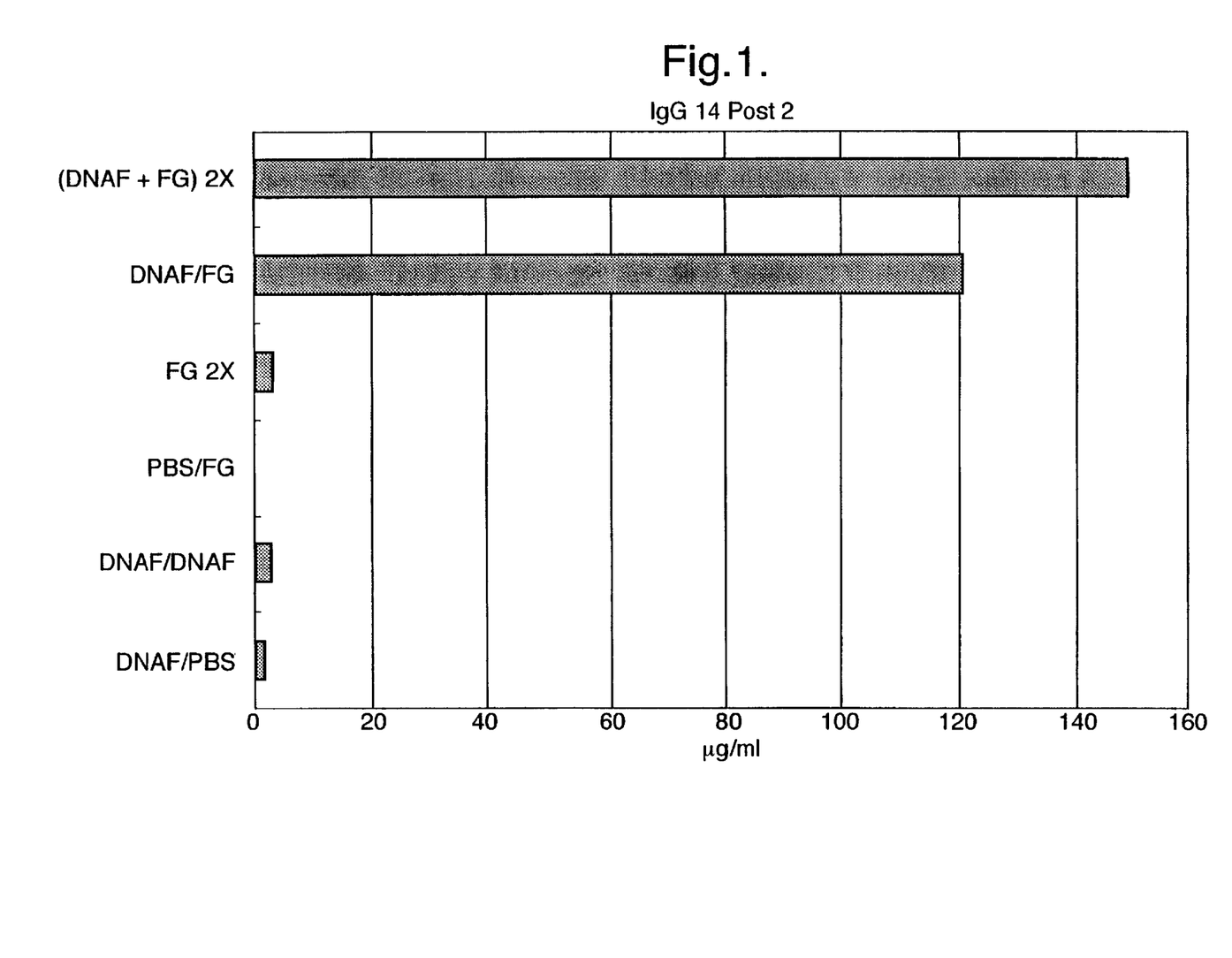
FIG. 1 (Ig 14 post 2) shows the serological responses in the immnunised animals 2 weeks after the booster injection. The combination of the two vaccine substrates strongly enhanced the amount of RSV-FG specific antibodies compared to those obtained by using the respective substrates separately ((DNA-F or FG protein) 2×).
Figure 2:
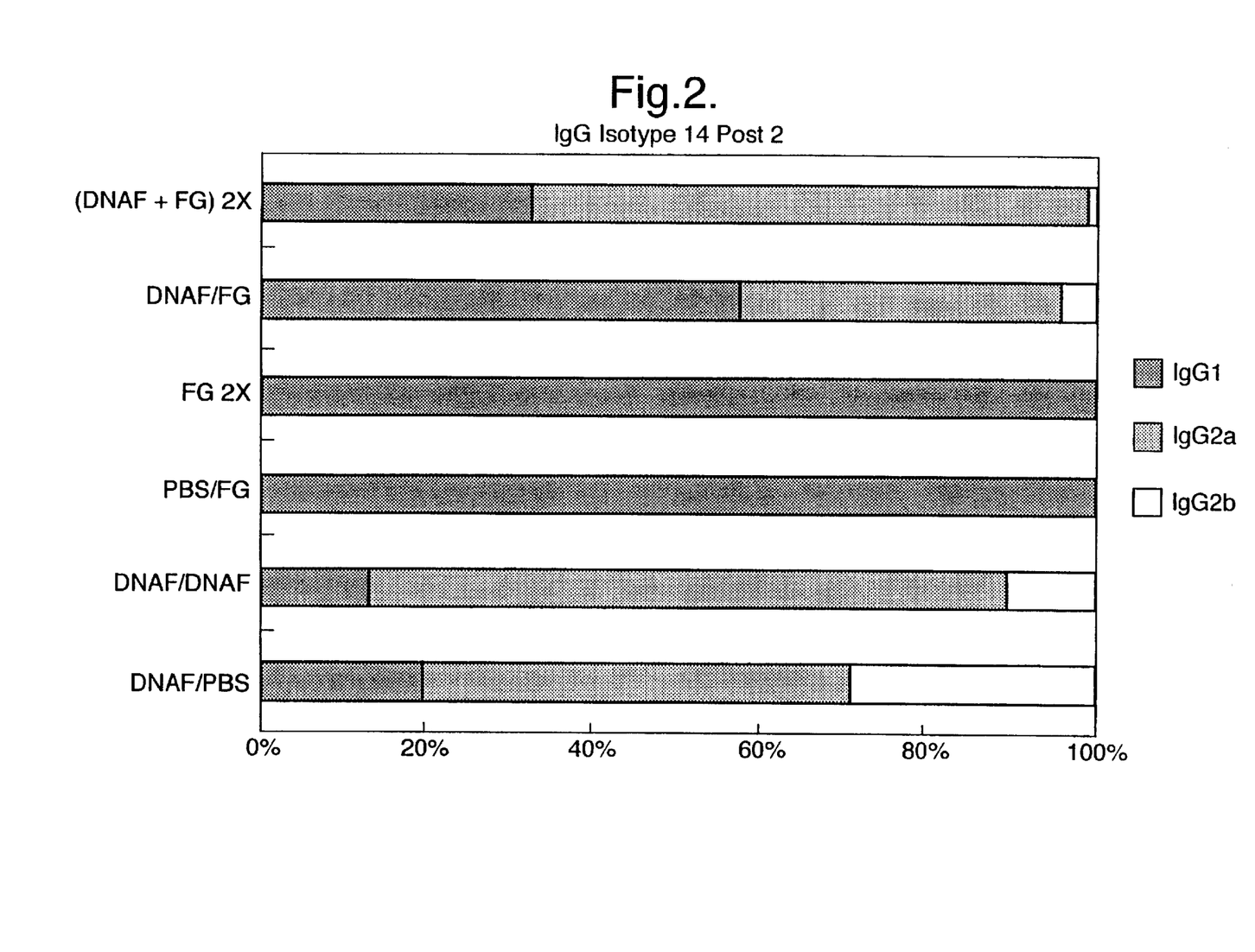
FIG. 2 (IgG isotype 14 post 2) shows the isotype distribution in the different vaccine groups. All the groups who did receive a DNA vaccine at the first injection have a strong content of IgG2a, indicative for a T helper response of type 1 (Th1), whereas the protein groups have a complete bias for the opposite, that is the IgG1 isotype typical for a Th2 type response.

FIG. 1 (Ig 14 post 2) shows the serological responses in the immunised animals 2 weeks after the booster injection. The combination of the two vaccine substrates strongly enhanced the amount of RSV-FG specific antibodies compared to those obtained by using the respective substrates separately ((DNAF or FG) 2×). Mixing the two vaccine compounds ((DNA+FG) 2×) was as effective as administering them in two separate injections by first priming with DNA and subsequent boosting with the protein alone (DNAF/FG). The total IgG titer of the mixed DNA/protein vaccine was much higher than the sum of the respective titers of the separate substrates indicating synergy upon mixing of the two vaccine substrates. FIG. 2 (IgG isotype 14 post 2) shows the isotype distribution in the different vaccine groups. All the groups who did receive a DNA vaccine at the first injection have a strong content of IgG2a, indicative for a T helper response of type 1 (Th1), whereas the protein groups have a complete bias for the opposite, that is the IgG1 isotype typical for a Th2 type response. Surprisingly, the mixed DNA+protein group also had a high level of the IgG2a isotype. This is unexpected since the immediate presence of the protein is supposed to direct the system towards a Th2 type response and would therefore impact on the DNA vaccine, which antigen is produced in vivo later on. The fact that increased antibody levels were obtained (FIG. 1) excludes the possibility that (i) the protein was not immunoreactive in this formulation and (ii) that the observed response was solely due to the DNA vaccine.

Example 4

Lymphoproliferative Responses upon Mixed Vaccine Administration

Induction of T helper cell activity and determination of the type of T helper cells were assessed as follows.

4.a. Protocols: In vitro Detection of FG-Specific Lymphoproliferation and Cytokine Production by Mice Spleen and Lymph Node Cells In vitro Stimulation Spleens and iliac lymph nodes were taken on day 15 after second immunization. Spleens and lymph nodes of animals belonging to the same group were pooled, gently triturated in medium 1 (RPMI 1640 completed with 2 mM L glutamine+5 $10^{-2}$ mM 2-mercaptoethanol+1 mM sodium pyruvate+1×non essential MEM amino acids+100 IU/ml penicillin+100 µg/ml streptomycin) (5 ml/spleen cells, 1 ml/lymph node cells) and centrifuged at 1200 rpm at RT for 10 minutes. Cell pellets were then resuspended in medium 1 (3 ml/spleen cells, 1 ml/lymph node cells), cell suspensions were counted on a multisizer counter and adjusted to $2\times10^6$ cells/ml in medium 2 (medium 1+1% heat inactivated normal mouse serum). 100 µl of these cell suspensions were added per well of U bottom 96 well plates. For specific restimulation, 100 µl of a serial, 2-fold dilution of purified FG (diluted in medium 2, ranging from 1.5 to 0.023 µg/per well) was used. Controls received 100 µl of medium only. Total stimulation was assessed by the addition of 100 µl ConA (Boehringer) at a final concentration of 5 µg/ml. All stimulation conditions were performed in triplicate. Plates were then incubated at 37° C. in a 5% $CO_2$ incubator for respectively 48 hrs (ConA total stimulation) or 72 h for FG specific restimulation. Thereafter, 100 µl of supernatant was withdrawn out of each well and replaced by fresh medium 1 supplemented with $^3$H-thymidine, 1 µCi/well (Amersham). Plates were incubated for another 18 to 24 hr at 37° C. in a 5% $CO_2$ incubator before being harvested. Thymidine incorporation was determined in a beta counter after cell lysis on nitrocellulose filters. The results are expressed in cpm (average of triplicates) for each restimulation condition.

Ctokine Detection

Spleen cells were processed in the same way as described here above except that they were adjusted to $5.10^6$ cells/ml in medium 3 (medium 1+10% heat inactivated FCS). 1 ml of these cell suspensions were added per well of a 24 well plate. Restimulation was done by adding purified FG antigen at 5 µg /ml (25 µl/well) to cells (medium was used as control). Plates were incubated at 37° C. in a 5% $CO_2$ incubator for 72 hr. Supernatants were withdrawn and tested for the presence of cytokines (IFNγ and IL-5) by Elisa. Maxisorp Nunc inmuunoplates were coated overnight at 4° C. with 50 µl/well of respectively 1.5 µg/ml rat monoclonal anti-mouse INFg (Genzyme) or 1 µg/ml rat monoclonal anti-mouse IL5 (Pharmingen) diluted in 0.1M bicarbonate buffer (pH 9.5). Saturation of plates was done for 1H at 37° C. with 100 µl/well of PBS BSA 1% Tween 20 (0.1%) NBCS 4% (saturation buffer). Then, standards were applied in row A by putting serial, 2-fold dilutions of either IFNg (Genzyme) or IL5 (Pharmingen) in saturation buffer (50 µl per well) starting at 2430 pg/ml or 2000 pg/ml, respectively. Samples were also serially, 2-fold diluted and added to the other rows of the plate. Plates were incubated for 1H30 at 37° C. Washing was done 3 times with PBS Tween 200.1%. Then, biotinylated goat anti-mouse INFg or IL5 antiserum (Genzyme and Pharmingen, respectively) diluted at a concentration of 0.5 or 1.0 µg/ml (respectively) in saturation buffer was incubated (50 µl/well) for 1H30 at 37° C. After 3 washings as above and subsequent addition for 30 min at 37° C. of AMDEX™ (Amersham) diluted 10000× in saturation buffer (50 µl/well), plates were washed 5 times and incubated for 10 min at room temperature (in darkness) with 50 µl/well of TMB substrate solution (Biorad). The reaction was stopped by adding 50 µl/well of $H_2SO_4$ (0.4N). Color intensity was read on a multiscan ELISA reader at wavelength 450/630 nm. The results are expressed in pg/ml IFNg or IL5 referring to the corresponding calibration curves using the 4 parameters method.

4.b. Results

Figure 3:
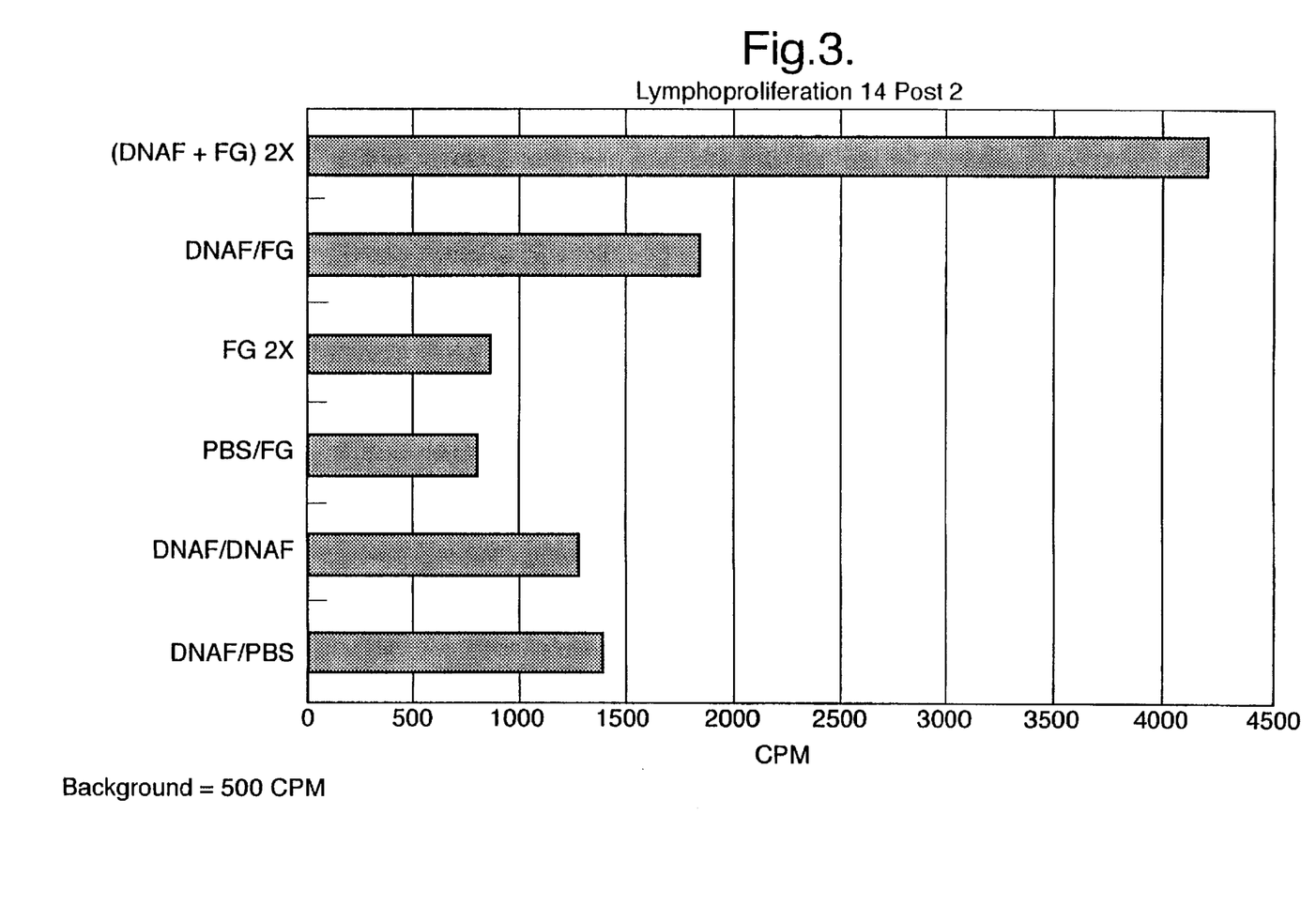
FIG. 3 (Lymphoproliferation) shows the lymphoproliferation of splenocytes from the different vaccine groups upon in vitro restimulation with the FG antigen.

FIG. 3 (Lymphoproliferation) shows the lymphoproliferation of splenocytes from the different vaccine groups upon in vitro restimulation with the FG antigen. Combining of the two vaccine compounds into one composition strongly increases this cellular response compared to monovalent (DNA or protein) vaccines or the DNA prime+protein boost immunisation. Table 1 (IFNg and IL5) shows the secretion of specific cytokines, IFN gamma and IL5 respectively, from the proliferating cells. The secretion of the Th2 cytokine, IL5, is low despite the strong lymphoproliferation of the mixed vaccine group. The IFNg/IL-5 ratio (Table 2), being a measure of the relative ratio of Th2 to Th1 type of T helper response, is consistent with the isotype distribution of this group (see FIG. 2) and further confirms the impact of the DNA in the mixed vaccine composition on the induction of a Th1 type of immune response.

Example 5

Cytotoxic T Cell Responses upon mixed Vaccine Administration

The induction of cytotoxic T cells (CTL's ) was determined as follows. Splenocytes were prepared as described in the previous section and $2.10^7$ spleen cells (effector cells) were grown in a 25 cm² flask with 10 ml of medium 3 (see example 4). These cells were stimulated for seven days (at 37° C., 7% $CO_2$) by the addition of RSV infected naive spleen cells (stimulator cells) at a ratio of 10/1 (E/S). These latter stimulator cells were obtained by infecting $2.10^6$ haemolyzed normal spleen cells with RSV (MOI 0.5) for 1 hr30 at 37° C. In preparation of the cytotoxicity assay, EMT6 syngeneic target cells (H2d mammary adenocarcinoma cells provided by Dr B. Rouse, Knoxville) were prepared as follows. $3.×10^6$EMT6 were collected by centrifugation, washed once with medium 1 and resuspended in 200 µl medium 1. Cells were infected with control vaccinia virus (PSC11, negative control) or a recombinant vaccinia virus expressing RSV-F at an MOI of 10 for 1 hr at 37° C. (vaccinia viruses were obtained from Dr. A. Bollen, Brussels). Infected cells were then adjusted to 1 ml with medium 3 are incubated overnight at 37° C. and 7% $Co_2$.

Infected cells were then washed, collected by centrifugation, and resuspended in 50 µl of FCS. 50 µl of radiolabeled sodium chromate (DuPont) at 370MBq/ml was added for 1 hr. Target cells were subsequently washed three times in medium 1, counted, and adjusted to a fmal concentration of $2.×10^4$ target cells/mil. For the cytotoxicity assay, Cr51 loaded EMT6 target cells were placed in the wells of a 96 wells microplate in the presence of different ratios of restimulated effector cells (E/T ratios of 100/1-30/1-10/1-3/1-1/1). All samples were done in duplicate at 100 µl/well. Microplates containing effectors and targets cells were then centrifuged for 5 minutes at 800 rpm and incubated for 4 hrs at 37° C. with $CO_2$. Thereafter, 50 µl of supernatants were transferred on a lumaplate (Packard), dried overnight and counted. Percentage of lysis was calculated as follows: (cpm sample-cpm spontaneous release)/(cpm max (triton3% lysis)-cpm spontaneous release)×100.

Results

Figure 4:
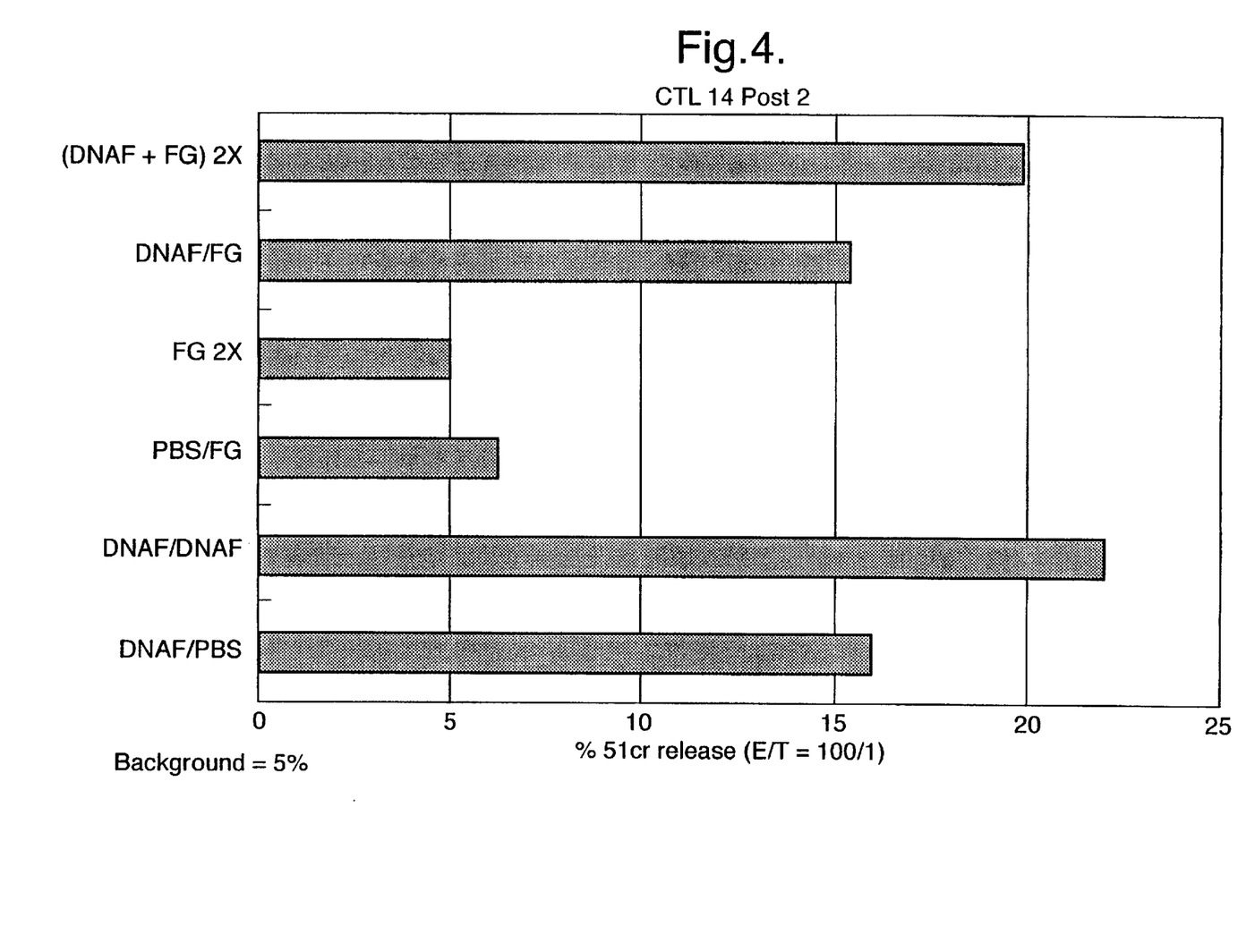
FIG. 4 shows the presence of CTL's in the different vaccine groups.

FIG. 4 shows the presence of CTL's in the different vaccine groups. As expected, DNA vaccination induces CTL whereas non-adjuvanted FG protein has a CTL value which is the same as the background lysis towards control target cells. A single administration of the DNA vaccine did prime for CTL induction and further boosting with either protein (alone) or DNA (alone) did not substantially increase this response. Mixing of the two vaccine compounds (DNA+ protein) did not impact on the induction of the CTL response by the DNA component, as CTL's could be detected. It is observed that admixing a DNA vaccine to a non-adjuvanted protein vaccine allows an extra dimension to its immune response, namely the induction of a CTL response.

Example 6

Enhanced Humoral Responses upon Mixed Vaccine Administration are Due to the Presence of a Specific Polynucleotide Encoding the Polypeptide of Interest It has been shown that in certain cases plasmid DNA can exert an adjuvant effect when co-administered with a heterologous polypeptide (Sato et al., Science 273:352–354 (1996)). To exclude that the observed enhancement of the humoral response as illustrated in Example 3 was due to an aspecific adjuvant effect of the plasmid DNA, following experiment was performed. Mice were immunised as described in Example 3 with the following preparations: 10 µg DNA-F, 10 µg DNA-F plus 2 µg FG (mixed antigens), 2 µg FG, or 10 µg pJA4304 plus 2 µg FG. This latter group resembles the mixed antigen group but with the difference that the plasmid DNA JA4304, having the same vector backbone as DNA-F, is not expressing the F polypeptide. Serological responses were analysed at 13 days after the second injection.

| ANTIGEN | Average IgG (µg/ml) | Standard Deviation |
|---|---|---|
| DNA-F 10 µg | 5.8 | 8.2 |
| DNA-F 10 µg + FG 2 µg | 60.8 | 20.5 |
| FG 2 µg | 5.1 | 5.5 |
| DNA-JA4304 + FG 2 µg | 4.4 | 3.9 |

From these results it is very clear that mixing the two specific antigen compositions (i.e. polypeptide FG and DNA-F) is strongly enhancing the humoral responses, and that a synergistic effect occurs. This enhancement is depending on the presence of a plasmid encoding the antigen since a similar, non-coding plasmid is not capable of enhancing the immune response.

Example 7

A Short Delayed Administration of a Polypeptide Antigen is Enhancing the Humoral Response of the Respective Polynucleotide Vaccine Polypeptide antigens have a more rapid presentation to the immune system than polynucleotide vaccines, since the encoded polypeptide has first to be expressed after uptake of the polynucleotide by the cell. A short delayed delivery of the polypeptide antigen presents the two immunogenic compositions (virtually) simultaneously to the immune system.

Mice were injected twice with the following immunogens: 30 μg DNA-gp120, 10 μg gp120 protein, 30 μg DNA-gp120 followed four days later by 10 μg gp120 protein (delayed protein delivery). Humoral responses and isotype distribution were determined essentially as described in Example 3 using gp120 protein to capture the anti-gp120 specific antibodies.

Figure 5:
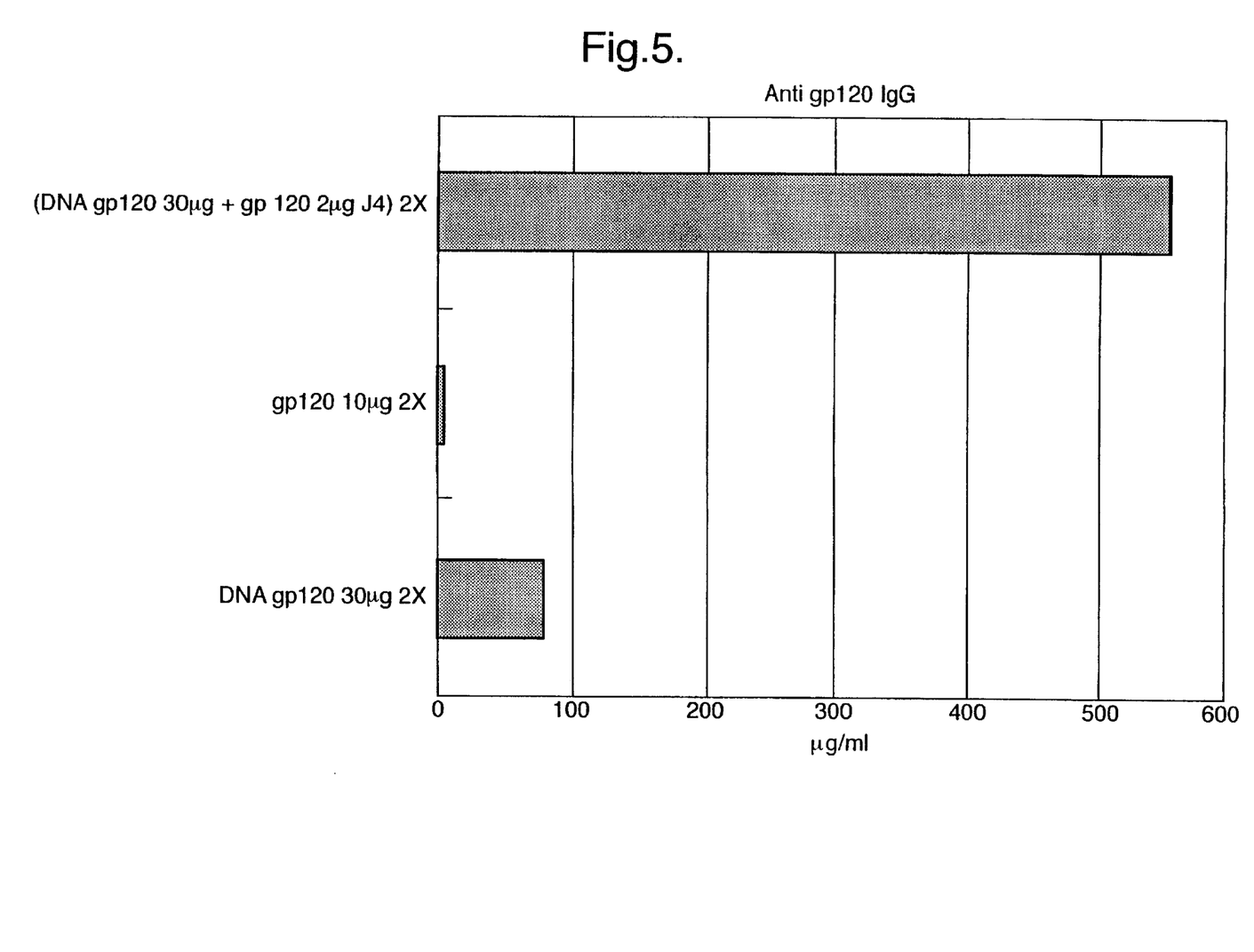
FIG. 5 shows the total anti-gp120 IgG titers 14 days after the second injection. IgG titers are strongly increased in the group which received the two antigen forms (polynucleotide and polypeptide). The polypeptide (protein) administration was delayed for four days.

FIG. 5 shows the total anti-gp120 IgG titers 14 days after the second injection. IgG titers are strongly increased in the group which received the two antigen forms (polynucleotide and polypeptide) where the protein administration was delayed for four days.

Figure 6:
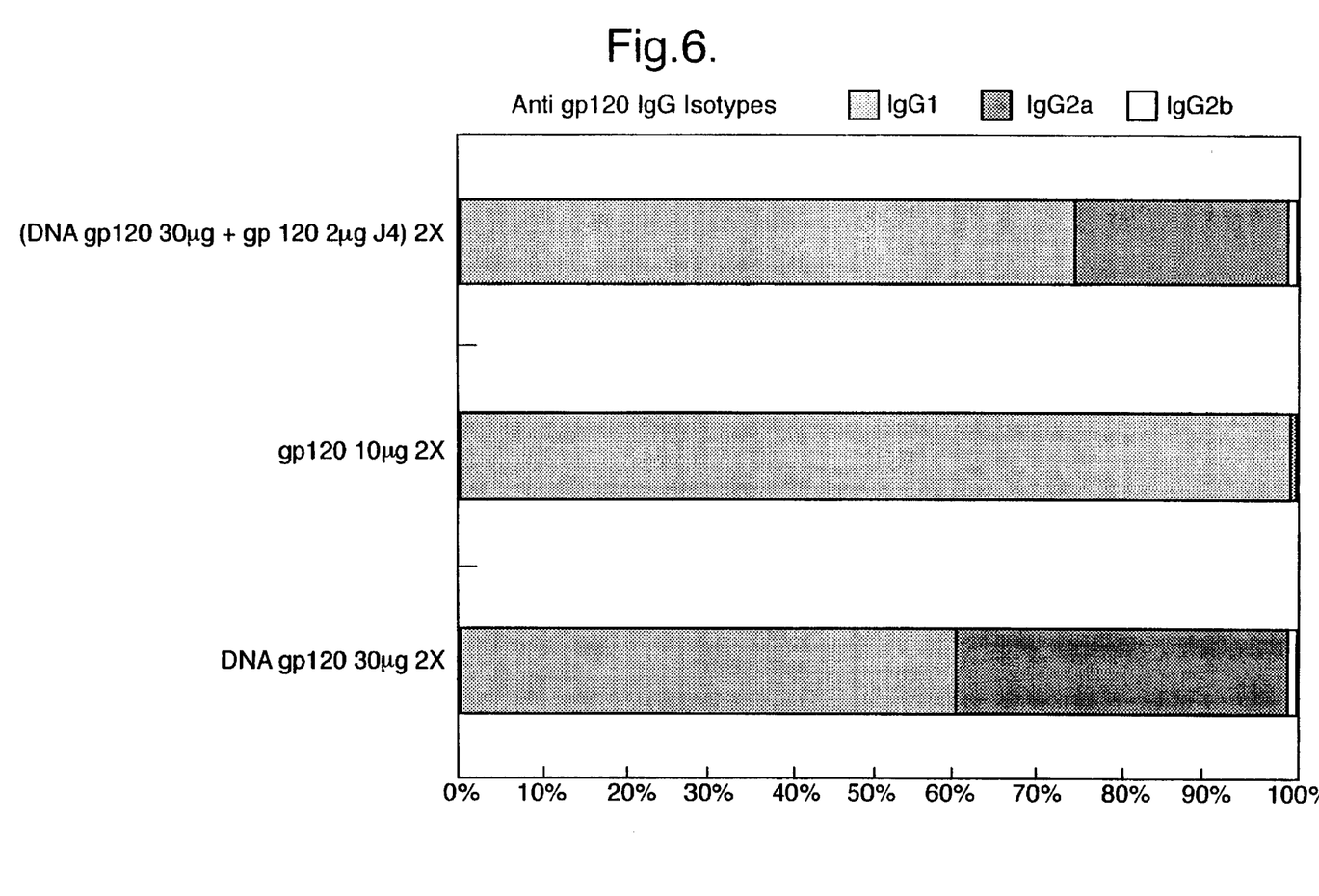
FIG. 6 shows the isotype distribution of anti-gp120 IgG titers. Delayed protein delivery maintains considerable IgG2a titers as observed for the DNA group, which is in contrast to the proteinnly group.

FIG. 6 shows the isotype distribution. As can be seen, delayed protein delivery maintains considerable IgG2a titers as observed for the DNA group, and this in strong contrast to the protein-only group.

Example 8

Preparation of Delayed-release Formulations

20 μg of the antigen gD2t was adsorbed onto 500 μg alum (aluminium hydroxide) in H$_2$O (final volume 90 μl). A solution of poly(capro-lactone)diol (average Mn 2000, softening temperature 50° C.) in ethanol (5 mg/ml: at 70° C.) was added to a ratio of 10:1 (polycaprolactone:alum) and temperature allowed to equilibrate to 25° C. This results in co-acervation of the polycaprolactone onto the particles of alum. The resulting coated particles were collected by centrifugation and washed with water.

For in vitro release kinetics, samples were prepared using radio-iodinated gD2t. The gD2t was iodinated using Iodogen (Pierce) by following the manufacturer's instructions. In vitro release kinetics were performed in 250 mM sodium phosphate. This medium causes instantaneous release of gD2t from alum. Polycaprolactone-coated alum was incubated in this medium at 37° C. for 8 days, and the release of antigen into the medium assayed by radioactivity measurements. For uncoated alum, the gD2t was released into the medium within 10 minutes. For polycaprolactone coated alum there was a slight (5–25%) release within the first 24 hours, followed by slow release over 8 days.

For in vivo studies the polycaprolactone-coated alum was mixed with DNA coding for gD at a ratio of 2 μg protein for 10 μg DNA.

Example 9

Increased Induction of Humoral Responses with Delayed Release Formulations

In order to allow simultaneous administration of both DNA and the corresponding protein antigen, delayed release formulations prepared as described above were tested. Mice were injected with the following antigen compositions (ALOH-PLC refers to polycaprolactone-coated alum containing gD2t):

| GROUP | DAY 0 | DAY 4 |
|---|---|---|
| 1 | 10 μg DNA-gD | |
| 2 | 10 μg DNA-gD | 2 μg gD/AlOH |
| 3 | | 2 μg gD/AlOH |
| 4 | 10 μg DNA-gD + 2 μg gD/AlOH-PLC | |
| 5 | 2 μg gD/AlOH-PLC | |

Humoral responses were determined 13 days after the first injection and are resented in the following Table:

| GROUP | Average titer (μg/ml) | Standard deviation | GMT |
|---|---|---|---|
| 1 | 5.7 | 3.8 | 4.4 |
| 2 | 17.3 | 19.3 | 11.1 |
| 3 | 1 | 1.1 | 0.7 |
| 4 | 16 | 8.3 | 13.9 |
| 5 | 0.9 | 0.5 | 0.9 |

As can be seen from these results, combined protein and DNA inimunisation leads to a stronger induction of the humoral response. The fact that titers of group 2 (protein administered 4 days after the DNA), and group 4 (delayed release formulation with simultaneous injection of DNA and formulated protein) are very similar, strongly indicates that delayed release of the protein has taken place and that the concomitant presence of the protein at the time of polynucleotide directed expression strongly enhances the induction of the humoral response induced by the DNA vaccine. As can be seen, virtually simultaneous presentation of the polypeptide from both vaccine compositions to the immune system can be achieved by a short delayed delivery of the polypeptide after the nucleic acid vaccination.

All publications, including but not limited to patents and patent applications, cited in this specification are herein incorporated by reference as if each individual publication were specifically and individually indicated to be incorporated by reference herein as though fully set forth.

While the preferred embodiments of the invention are illustrated by the above, it is to be understood that the invention is not limited to the precise instructions herein disclosed and that the right to all modifications coming within the scope of the following claims is reserved.

TABLE 1

| | Prime Boost RSV 14 Post 2 | | | | | | | |
|---|---|---|---|---|---|---|---|---|
| | IgG | IgG1 | IgG2a | IgG2b | Prolif | IL5 | INFg | CTL |
| DNAF/PBS | 1 | 19 | 51 | 29 | 1387 | 300 | 2406 | 16 |
| DNAF/DNAF | 2 | 13 | 77 | 10 | 1272 | 300 | 1069 | 22 |
| PBS/FG | 0 | 100 | 0 | 0 | 807 | 300 | 391 | 6 |
| FG 2X | 2 | 100 | 0 | 0 | 861 | 367 | 360 | 5 |
| DNAF/FG | 120 | 57 | 39 | 4 | 1837 | 2195 | 3272 | 15 |
| (DNAF + FG) 2X | 149 | 32 | 67 | 1 | 4190 | 300 | 1553 | 20 |
| | μg/ml | % | % | % | CPM | pg/ml | pg/ml | % Cr51 release |

TABLE 2

| | RSV 14 Post 2 | | |
|---|---|---|---|
| | INFg | IL5 | Ratio INFg/IL5 |
| DNAF/PBS | 2406 | 300 | 8.02 |
| DNAF/DNAF | 1069 | 300 | 3.56 |
| PBS/FG | 391 | 300 | 1.30 |
| FG 2X | 360 | 367 | 0.98 |
| DNAF/FG | 3272 | 2195 | 1.49 |
| (DNAF + FG) 2X | 1553 pg/ml | 300 pg/ml | 5.18 |

What is claimed is:

1. A method for enhancing an immune response in an subject wherein the immune response is induced by administration of a polynucleotide, the method comprising the steps of:

(1) administering a polynucleotide encoding a polypeptide; and (2) administering the polypeptide encoded by the polynucleotide administered in (1)

wherein the polypeptide is administered 1–10 days after the polynucleotide is administered and wherein the method results in an increase in the immune response to the polypeptide as measured by one or more members selected from the group consisting of (i) total antibody titer, (ii) lymphoproliferation and (iii) cyctotoxic T cell level when compared to the immune response induced by administration of the polynucleotide in the absence of administration of the polypeptide.

2. The method of claim 1 wherein the polypeptide is administered 3–7 days after the polynucleotide is administered.

* * * * *